(12) United States Patent
Oppenheim et al.

(10) Patent No.: US 11,103,699 B1
(45) Date of Patent: Aug. 31, 2021

(54) NERVE STIMULATION GARMENT

(71) Applicant: ZIDA LLC, Gainesville, VA (US)

(72) Inventors: Andrew Oppenheim, Gainesville, VA (US); Jerome Orlin, Beit Horon (IL)

(73) Assignee: ZIDA LLC, Gainesville, VA (US)

( * ) Notice: Subject to any disclaimer, the term of this patent is extended or adjusted under 35 U.S.C. 154(b) by 0 days.

(21) Appl. No.: 17/094,853

(22) Filed: Nov. 11, 2020

(51) Int. Cl.
*A61N 1/36* (2006.01)
*A61N 1/04* (2006.01)
*A41B 11/00* (2006.01)

(52) U.S. Cl.
CPC .......... *A61N 1/36007* (2013.01); *A41B 11/00* (2013.01); *A61N 1/0456* (2013.01); *A61N 1/0484* (2013.01); *A61N 1/36034* (2017.08)

(58) Field of Classification Search
CPC .......... A61N 1/36007; A61N 1/36034
USPC .......... 607/59
See application file for complete search history.

(56) References Cited

U.S. PATENT DOCUMENTS

| 9,254,382 | B2 | 2/2016 | Ahmad et al. |
| 9,630,004 | B2 | 4/2017 | Rajguru et al. |
| 2014/0228927 | A1* | 8/2014 | Ahmad ............... A61H 39/002 607/148 |
| 2016/0074671 | A1 | 3/2016 | Burnett et al. |
| 2020/0171304 | A1 | 6/2020 | Simon et al. |
| 2020/0270775 | A1 | 8/2020 | Oppenheim |

OTHER PUBLICATIONS

Endotherapeutics, "Urgent PC PTNS for OAB Instructional Video", p. 1, Jul. 28, 2019 https://www.youtube.com/watch?v=vN4es_S5uzg&feature=emb_logo.
Noble Biomaterials, "Electrostatic Discharge (ESD) Solutions", pp. 1-4, year 2021 downloaded from https://noblebiomaterials.com/x-static/.
Swicofil AG, "Plasma Metal Coated Yarn", pp. 1-4, Apr. 2, 2019.
Statex, "Silver Heals", pp. 1-3, year 2020.
DEXMAT, "DEXMAT Makes High Performance Galvom Products from Carbon Nanoubes (CNTS)", pp. 1-6, year 2018.

* cited by examiner

*Primary Examiner* — Nadia A Mahmood
(74) *Attorney, Agent, or Firm* — Kligler & Associates Patent Attorneys Ltd

(57) ABSTRACT

Apparatus for electrical stimulation includes a garment, including an elastic knitted fabric, which is shaped and sized to fit snugly over a part of a body of a human subject, and at least one electrode, which includes an electrically-conductive yarn interknitted with the elastic knitted fabric in a predefined location so as to make electrical contact with a skin surface of the human subject when the garment is worn on the body. Stimulation circuitry is configured to apply an alternating electrical current to the at least one electrode.

21 Claims, 2 Drawing Sheets

NERVE STIMULATION GARMENT

FIELD OF THE INVENTION

The present invention relates generally to wearable electronic devices, and particularly to methods and devices for transcutaneous nerve stimulation.

BACKGROUND

Overactive bladder is a common condition, characterized by a frequent feeling of needing to urinate, often accompanied by urinary incontinence. Incidence of the condition increases with age. A variety of treatments are available, ranging from exercise and behavioral methods to medications and invasive medical procedures.

Some methods for treating overactive bladder use electrical stimulation of the tibial or sacral nerve. For example, Percutaneous Tibial Nerve Stimulation (PTNS) is a type of electro-acupuncture that indirectly stimulates the nerves responsible for bladder and pelvic floor function. During PTNS treatment, a needle electrode is inserted into the patient's ankle near the tibial nerve, and an electrical stimulator is connected to apply mild electrical pulses to the electrode. These pulses travel up the tibial nerve to the sacral nerve plexus, which controls bladder function, and thus relieve the urge to urinate.

Devices for noninvasive, transcutaneous electrical stimulation of the tibial nerve are also known in the art. For example, U.S. Pat. No. 9,254,382 describes an electro-acupuncture device for controlling overactive bladder. The device includes a housing, circuitry for generating electro-acupuncture stimulus disposed within the housing, and at least one strap for securing the housing to the ankle. The device also includes a pair of D-shaped electrodes within the bottom outer surface of the housing. The housing is flexible, with a low profile, and is shaped so that it is conformal to a person's ankle. When the device is strapped to a patient's ankle, the electrodes contact the ankle and provide electric stimulation to the tibial nerve within the ankle.

SUMMARY

Embodiments of the present invention that are described hereinbelow provide garments with integral, fabric-based electrodes, as well as methods for producing and using such garments.

There is therefore provided, in accordance with an embodiment of the invention, apparatus for electrical stimulation, which includes a garment, including an elastic knitted fabric, which is shaped and sized to fit snugly over a part of a body of a human subject. The apparatus includes at least one electrode includes an electrically-conductive yarn interknitted with the elastic knitted fabric in a predefined location so as to make electrical contact with a skin surface of the human subject when the garment is worn on the body. Stimulation circuitry is configured to apply an alternating electrical current to the at least one electrode.

In some embodiments, the garment includes a sock or stocking, which is shaped and sized to fit over a foot of the human subject. Typically, the at least one electrode includes a first electrode located between a heel and a toe of the garment, and a second electrode located on an ankle of the garment. In the disclosed embodiments, the stimulation circuitry is configured to apply the electrical current with a frequency and amplitude selected to stimulate a tibial nerve in the foot of the human subject. In one embodiment, the stimulation circuitry is configured to output the electrical current as a bipolar square wave, and the amplitude of the square wave is between 10 and 150 mA.

In some embodiments, the electrically-conductive yarn includes an elastomer with an electrically-conductive coating. In one embodiment, the electrically-conductive coating is selected from a group of coatings consisting of metal coatings and graphene coatings. Alternatively or additionally, the electrically-conductive yarn includes an elastomeric monofilament and an electrically-conductive thread crocheted around the elastomeric monofilament.

Additionally or alternatively, the apparatus includes a connector, which is configured to mechanically connect the stimulation circuitry to the garment while electrically connecting the stimulation circuitry to the at least one electrode. In a disclosed embodiment, the apparatus includes a wire running through the elastic knitted fabric from the connector to the at least one electrode.

Additionally or alternatively, the connector includes a pair of magnetic snaps. In one embodiment, the magnetic snaps include a magnetic stud, fixed to the garment in a first location, with a first magnetic polarity and a magnetic socket, fixed to the garment in a second location, adjacent to the first location, with a second magnetic polarity opposite to the first magnetic polarity.

Further additionally or alternatively, the stimulation circuitry includes a housing, which is mechanically connected to the garment by the connector, and an electrical power source contained in the housing.

There is also provided, in accordance with an embodiment of the invention, a garment, including an elastic knitted fabric, which is shaped and sized as a sock or stocking to fit snugly over a foot of a human subject. At least one electrode includes an electrically-conductive yarn interknitted with the elastic knitted fabric in a predefined location so as to make electrical contact with a skin surface of the human subject when the garment is worn on the foot.

There is additionally provided, in accordance with an embodiment of the invention, a method for electrical stimulation, which includes providing a garment, including an elastic knitted fabric, which is shaped and sized to fit snugly over a part of a body of a human subject, with at least one electrode, including an electrically-conductive yarn interknitted with the elastic knitted fabric in a predefined location so as to make electrical contact with a skin surface of the human subject when the garment is worn on the body. An alternating electrical current is applied to the at least one electrode so as to stimulate a nerve in the body.

There is further provided, in accordance with an embodiment of the invention, a method for producing a garment. The method includes knitting an elastic fabric to produce a sock or stocking, which is shaped and sized to fit snugly over a foot of a human subject. An electrically-conductive yarn is interknitted with the elastic knitted fabric in at least one predefined location so as to produce at least one electrode, which is configured to make electrical contact with a skin surface of the human subject when the sock or stocking is worn on the foot. An electrical connection is provided to the at least one electrode within the knitted elastic fabric.

The present invention will be more fully understood from the following detailed description of the embodiments thereof, taken together with the drawings in which:

DETAILED DESCRIPTION OF EMBODIMENTS

Figure 1:
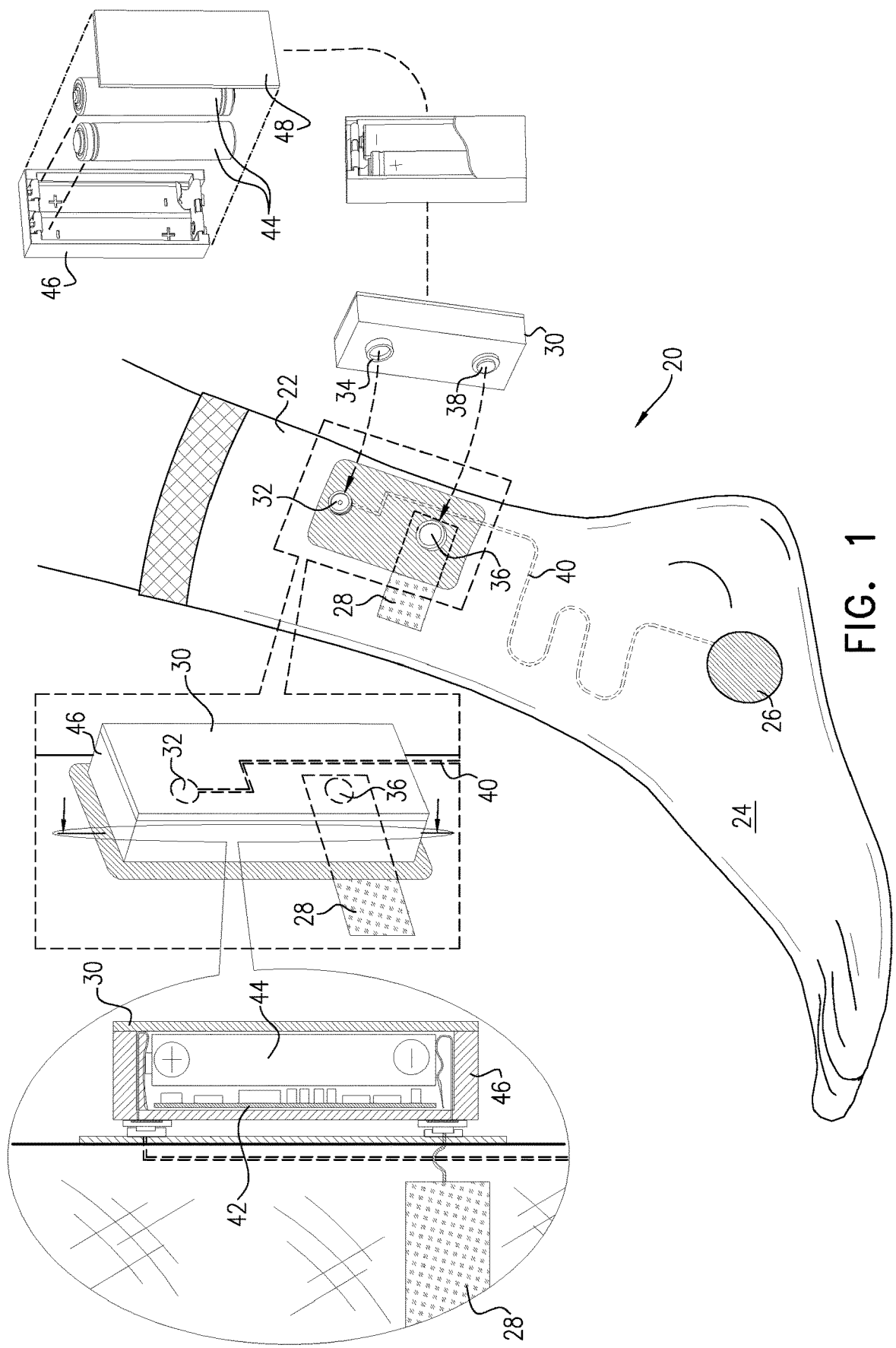
FIG. 1 is schematic pictorial illustration of an electrical stimulation sock, in accordance with an embodiment of the invention.

As explained above, electrical stimulation of the tibial nerve is a safe, effective treatment in many cases of overactive bladder and urge incontinence. This treatment modality has not been widely adopted, however, due to difficulties in administering the treatment in the home environment: Percutaneous administration requires a medical professional to insert a needle electrode through the skin, while transcutaneous administration requires that patch electrodes be glued to the skin in the appropriate locations, typically by a medical professional. Both of these options restrict the patient's mobility during treatment. Proper placement of the electrodes is challenging, particularly for elderly patients.

Embodiments of the present invention that are described herein address these problems by providing a garment, such as a sock or stocking, with one or more integrated fabric electrodes. The locations of the electrodes are chosen so that when the patient is wearing the garment, the electrodes contact the skin at precise positions close to the nerves that are to be stimulated. The patient is thus able to position the electrodes properly simply by putting on the garment. Stimulation circuitry, which is built into the garment or can be easily attached to the garment, applies an alternating electrical current to the electrodes with a frequency and amplitude selected so as to stimulate the nerve.

In the disclosed embodiments, the garment comprises an elastic knitted fabric, which is shaped and sized to fit snugly over the appropriate part of the body of a human subject (for example, over the foot for purposes of tibial nerve stimulation). The electrode or electrodes comprise an electrically-conductive yarn, which is interknitted with the elastic knitted fabric at locations at which the electrodes are to contact the subject's skin surface when the garment is worn on the body. In the context of the present description and in the claims, the term "interknitted" means that at least some of the loops of the knitted electrically-conductive yarn are intertwined with the loops of the yarn in the knitted fabric of the garment. (Not all of the loops of electrically-conductive yarn are necessarily intertwined with the yarn of the knitted fabric; rather, within the electrodes, the loops of electrically-conductive yarn may be intertwined with one another.) In the disclosed embodiments, the electrically-conductive yarn comprises an elastomer with an electrically-conductive coating. This sort of electrically-conductive yarn can be knitted together with the yarn of the garment using conventional knitting machines and processes, similar to those used in creating jacquard patterns using yarns of different colors to create decorative patterns in a garment.

The example embodiment that is shown in the figures and described in detail hereinbelow is directed to a sock with two electrodes, for use in tibial nerve stimulation, particularly for treatment of overactive bladder syndrome. Alternatively, the principles of the present invention may be applied in producing garments with one, two, three or more interknitted electrodes, including not only socks and stockings, but also garments that fit over other parts of the body, such as the hands, arms, head, neck and torso. All such alternative applications and implementations are considered to be within the scope of the present invention.

Figure 2:
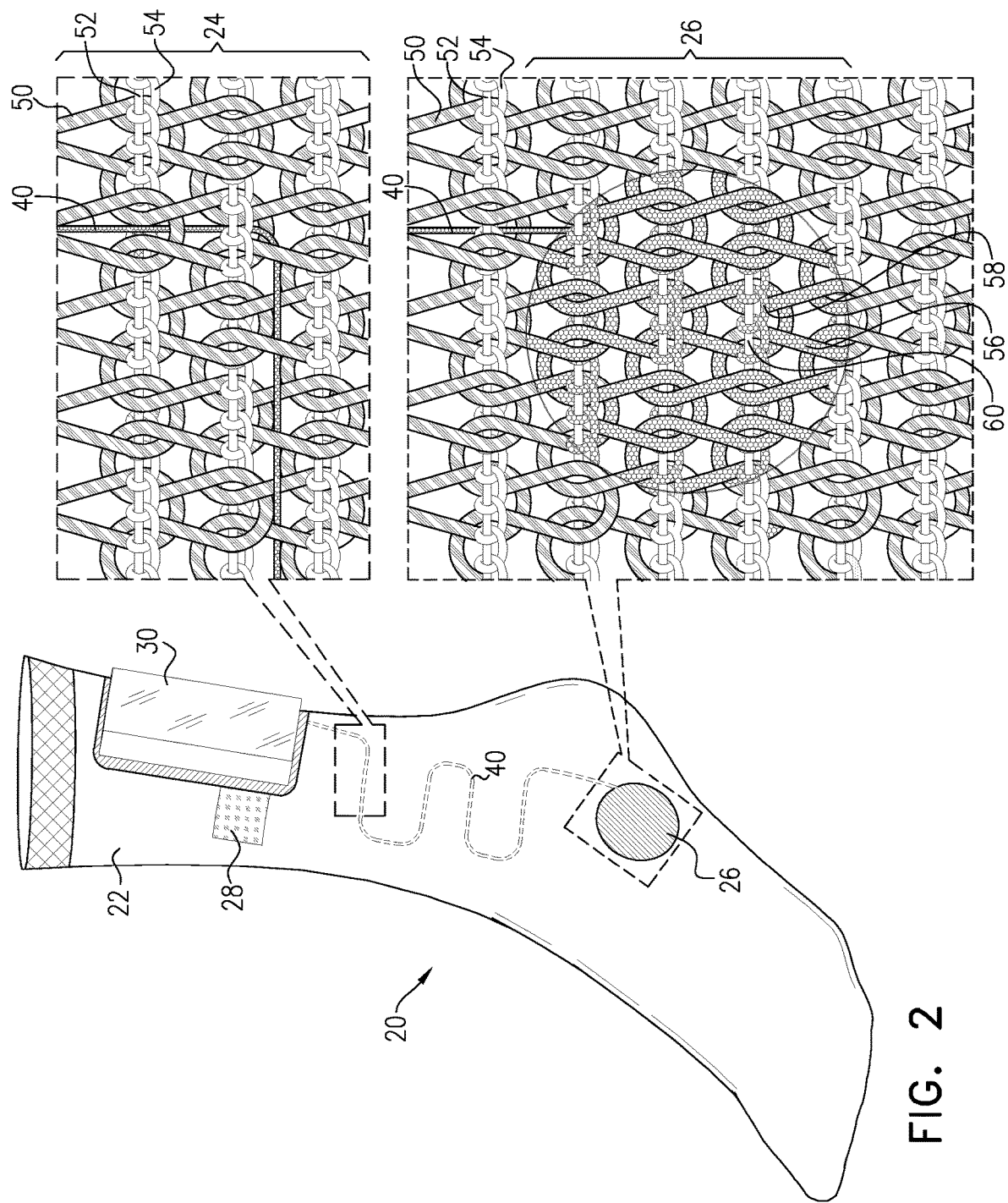
FIG. 2 is a schematic detail view of knit fabric in the sock of FIG. 1, in accordance with an embodiment of the invention.

Reference is now made to FIGS. 1 and 2, which schematically illustrate apparatus 20 for electrical stimulation, in accordance with an embodiment of the invention. As shown in FIG. 1, apparatus 20 comprises an electrical stimulation sock 22, while FIG. 2 shows a knitted fabric 24 in sock 22, along with interknitted electrodes 26 and 28. The figures show sock 22 fitted over the foot of a human subject. (A stocking could be produced and fitted in similar fashion.)

In the pictured embodiment, electrode 26 is located between the heel and the toe of sock 22, while electrode 28 is located on the ankle of the sock. For effective stimulation of the tibial nerve, electrode 26 is typically between 5 and 10 cm forward from the heel, while electrode 28 is between 7 and 12.5 cm above the heel, depending on the size of the foot and the corresponding size of the sock. Alternatively, other electrode placements may be used.

An electronic module 30 comprising stimulation circuitry 42 applies an electrical current between electrodes 26 and 28 with a frequency and amplitude selected to stimulate the tibial nerve. For this purpose, the electrical current typically has the form of a bipolar wave, with a frequency in the range of 10-120 Hz and a current amplitude that is adjustable between 1 and 150 mA (though currents are generally in the range of 10-150 mA). More specifically, a square wave with a frequency of about 20 Hz and an amplitude in the range of 50-60 mA is believed to be therapeutically effective. Alternatively, other waveforms, with different frequency and amplitude characteristics, may be applied. Stimulation circuitry 42 comprises components that are known in the art for the purpose or electrical waveform generation.

Stimulation circuitry 42 is contained in a housing 46 together with an electrical power source, such as one or more batteries 44. Housing 46 typically comprises a suitable plastic enclosure, with a removable cover 48 to enable replacement of batteries 44. Alternatively or additionally, batteries 44 may be rechargeable and installed permanently in housing 46. In this latter case, housing 46 contains a suitable charging plug and/or a coil for inductive charging of the batteries (not shown), as is known in the art.

In the pictured embodiment, electronic module 30 is mechanically and electrically connected to sock 22 by a connector made up of two pairs of magnetic snaps, including magnetic studs 32 and 38 and magnetic sockets 34 and 36. Stimulation circuitry 42 is electrically connected to electrodes 26 and 28 via these snaps, which are electrically conductive. Specifically, in the present example, electrode 28 is directly connected to socket 36, while a wire 40 running through fabric 24 connects stud 32 to electrode 26. (Wire 40 may be either elastic or non-elastic.) Typically, studs 32 and 38 have one magnetic polarity, while sockets 34 and 36 have the opposite polarity to the studs, thus ensuring that module 30 can be connected to sock 22 only in the correct orientation. (In the reverse orientation, the two studs and the two sockets will repel one another.) This sort of connection makes it easy and foolproof for the patient to attach and detach electronic module 30, so that the same electronic module can be used with multiple different socks, and also allows the socks to be laundered without compromising the stimulation circuitry.

Alternatively, electronic module 30 may be permanently fixed to sock 22, with appropriate mechanical encapsulation to protect stimulation circuitry 42 when the sock is laundered.

As shown in the insets in FIG. 2, fabric 24 of sock 22 comprises knitted strands of a yarn 50, for example a suitable cotton, wool or synthetic yarn. In the pictured example, the courses of knitted loops of yarn 50 are interlaid with strands of an elastic yarn, made of an elastomer 52, such as Lycra®, covered by a synthetic thread 54, such as nylon thread. The elasticity of fabric 24 causes sock 22 to fit snugly around the subject's foot. ("Snug" in this context means that the garment fits tightly enough around the part of the subject's body in question so that the fabric will expand and conform to the shape of the body part when the subject wears the garment.)

Within the area of electrode 26, an electrically-conductive yarn 56 is interknitted with the loops of yarn 50. Yarn 56 typically comprises an elastomer, such as nylon or another suitable polymer, with an electrically conductive coating. This coating may comprise, for example, a metal, such as silver or gold, or a carbon-based conductor, such as graphene. Suitable yarns of this sort include, for example, X-STATIC filament yarns, produced by Noble Biomaterials (Scranton Pa.); and metal-coated yarns available from Swicofil AG (Emmenbrücke, Switzerland). Yarn 56 is electrically connected to electronic module 30 by wire 40 running through fabric 24.

Additionally or alternatively, the courses of knitted loops of yarn 56 are interlaid with strands of an elastic conductive yarn, which is made of an elastomeric monofilament 60 with an electrically-conductive thread 58 crocheted around the monofilament. Monofilament 60 may comprise an elastic polyurethane fiber, such as Lycra®, for example, or another polymer or natural rubber thread. Electrically-conductive thread 58 may comprise a silver-coated nylon thread, for example, such as silver threads available from Statex (Bremen, Germany). Alternatively, thread 58 may comprise a metal monofilament or a nanocarbon-impregnated synthetic fiber, such as threads and yarns produced by DexMat Inc. (Houston, Tex.). Yarn 56 may similarly be made from materials of these sorts. Further details of conductive yarns and methods for producing such yarns are described in U.S. patent application Ser. No. 16/284,181, filed Feb. 25, 2019, which is assigned to the assignee of the present patent application and whose disclosure is incorporated herein by reference.

Although the lower inset in FIG. 2 refers specifically to electrode 26, electrode 28 may be interknitted with fabric 24 in like fashion. Electrodes 26 and 28 may be round or rectangular, as shown in the present figures, or they may have any other suitable shape that can be made by interknitting. As noted earlier, this sort of interknitting is commonly used in creating decorative patterns in knitted fabrics, and electrically-conductive yarns, such as yarn 56, may thus be interknitted with fabric 24 to define electrodes using machinery and methods that are known in the art. Magnetic studs 32 and sockets 36, as well as other suitable conductive connectors, are likewise widely available in the garment industry (although they are conventionally used only as mechanical connectors, rather than electrical as in the present embodiments).

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for electrical stimulation, comprising:
a garment, comprising an elastic knitted fabric, which is shaped and sized to fit snugly over a part of a body of a human subject;
at least one electrode, comprising an electrically-conductive yarn interknitted with the elastic knitted fabric in a predefined location so as to make electrical contact with a skin surface of the human subject when the garment is worn on the body, wherein the electrically-conductive yarn comprises an elastomer with an electrically-conductive coating, which is selected from a group of coatings consisting of metal coatings and graphene coatings; and
stimulation circuitry, configured to apply an alternating electrical current to the at least one electrode.

2. The apparatus according to claim 1, wherein the garment comprises a sock or stocking, which is shaped and sized to fit over a foot of the human subject.

3. The apparatus according to claim 2, wherein the at least one electrode comprises a first electrode located between a heel and a toe of the garment, and a second electrode located on an ankle of the garment.

4. The apparatus according to claim 3, wherein the stimulation circuitry is configured to apply the electrical current with a frequency and amplitude selected to stimulate a tibial nerve in the foot of the human subject.

5. The apparatus according to claim 4, wherein the stimulation circuitry is configured to output the electrical current as a bipolar square wave, and the amplitude of the square wave is between 10 and 150 mA.

6. Apparatus for electrical stimulation, comprising:
a garment, comprising an elastic knitted fabric, which is shaped and sized to fit snugly over a part of a body of a human subject;
at least one electrode, comprising an electrically-conductive yarn interknitted with the elastic knitted fabric in a predefined location so as to make electrical contact with a skin surface of the human subject when the garment is worn on the body, wherein the electrically-conductive yarn comprises an elastomeric monofilament and an electrically-conductive thread crocheted around the elastomeric monofilament; and
stimulation circuitry, configured to apply an alternating electrical current to the at least one electrode.

7. The apparatus according to claim 1, and comprising a connector, which is configured to mechanically connect the stimulation circuitry to the garment while electrically connecting the stimulation circuitry to the at least one electrode.

8. The apparatus according to claim 7, and comprising a wire running through the elastic knitted fabric from the connector to the at least one electrode.

9. The apparatus according to claim 7, wherein the connector comprises a pair of magnetic snaps.

10. The apparatus according to claim 9, wherein the magnetic snaps comprise a magnetic stud, fixed to the garment in a first location, with a first magnetic polarity and a magnetic socket, fixed to the garment in a second location, adjacent to the first location, with a second magnetic polarity opposite to the first magnetic polarity.

11. The apparatus according to claim 7, wherein the stimulation circuitry comprises a housing, which is mechanically connected to the garment by the connector, and an electrical power source contained in the housing.

12. A garment, comprising:
an elastic knitted fabric, which is shaped and sized as a sock or stocking to fit snugly over a foot of a human subject;
at least one electrode, comprising an electrically-conductive yarn interknitted with the elastic knitted fabric in a predefined location so as to make electrical contact with a skin surface of the human subject when the garment is worn on the foot; and a connector, comprising a pair of magnetic snaps, which is configured to mechanically connect an electronic module to the garment while electrically connecting the electronic module to the at least one electrode.

13. The garment according to claim 12, wherein the at least one electrode comprises a first electrode located between a heel and a toe of the sock or stocking, and a second electrode located on an ankle of the sock or stocking.

14. A method for electrical stimulation, comprising:
providing a garment, comprising an elastic knitted fabric, which is shaped and sized to fit snugly over a part of a body of a human subject, with at least one electrode, comprising an electrically-conductive yarn interknitted with the elastic knitted fabric in a predefined location so as to make electrical contact with a skin surface of the human subject when the garment is worn on the body and a connector, comprising a pair of magnetic snaps, which is configured to mechanically connect an electronic module to the garment while electrically connecting the electronic module to the at least one electrode; and
applying an alternating electrical current from the electronic module to the at least one electrode so as to stimulate a nerve in the body.

15. The method according to claim 14, wherein the garment comprises a sock or stocking, which is shaped and sized to fit over a foot of the human subject.

16. The method according to claim 15, wherein the at least one electrode comprises a first electrode located between a heel and a toe of the garment, and a second electrode located on an ankle of the garment, and wherein the alternating electrical current is applied with a frequency and amplitude selected to stimulate a tibial nerve in the foot of the human subject.

17. The apparatus according to claim 6, wherein the garment comprises a sock or stocking, which is shaped and sized to fit over a foot of the human subject.

18. The apparatus according to claim 17, wherein the at least one electrode comprises a first electrode located between a heel and a toe of the garment, and a second electrode located on an ankle of the garment.

19. The apparatus according to claim 18, wherein the stimulation circuitry is configured to apply the electrical current with a frequency and amplitude selected to stimulate a tibial nerve in the foot of the human subject.

20. The apparatus according to claim 6, and comprising a connector, which is configured to mechanically connect the stimulation circuitry to the garment while electrically connecting the stimulation circuitry to the at least one electrode.

21. The apparatus according to claim 20, wherein the connector comprises a pair of magnetic snaps.

\* \* \* \* \*